US006579306B1

(12) United States Patent
Voelker et al.

(10) Patent No.: US 6,579,306 B1
(45) Date of Patent: Jun. 17, 2003

(54) EXPANSION CATHETER FOR BYPASS SURGERY INCLUDING TWO EXPANSION ZONES AND THEREBETWEEN AN INTERMEDIATE CONSTRICTION

(75) Inventors: Wolfram Voelker, Weinheim (DE); Georg Ertl, Mannheim (DE)

(73) Assignees: Klinikum Mannheim gGmbH, Manneheim (DE); Universitaet Heidelberg, Heidelberg (DE)

( * ) Notice: Subject to any disclaimer, the term of this patent is extended or adjusted under 35 U.S.C. 154(b) by 0 days.

(21) Appl. No.: 09/582,725
(22) PCT Filed: Jan. 13, 1999
(86) PCT No.: PCT/EP99/00140
§ 371 (c)(1),
(2), (4) Date: Jun. 30, 2000
(87) PCT Pub. No.: WO99/35975
PCT Pub. Date: Jul. 22, 1999

(30) Foreign Application Priority Data

Jan. 14, 1998 (DE) .......................... 198 01 076

(51) Int. Cl.$^7$ .................................................. A61F 2/06
(52) U.S. Cl. ..................................... 623/1.11; 623/1.23
(58) Field of Search .......................... 623/1.11, 1.23, 623/1.3, 1.31, 1.12; 606/194, 191; 604/106, 107

(56) References Cited

U.S. PATENT DOCUMENTS 4,733,665 A * 3/1988 Palmaz ....................... 604/104
5,197,978 A * 3/1993 Hess ........................... 606/194
5,514,176 A * 5/1996 Bosley, Jr. .................. 606/156
5,683,449 A * 11/1997 Marcade ..................... 128/898
5,725,547 A * 3/1998 Chuter ........................ 606/191
5,741,333 A * 4/1998 Frid ........................... 623/1.18
5,855,565 A * 1/1999 Bar-Cohen et al. ......... 604/104
5,876,448 A * 3/1999 Thompson et al. ......... 606/191
6,120,534 A * 9/2000 Ruiz ........................... 606/194

FOREIGN PATENT DOCUMENTS

DE 3235974 9/1982
DE 19509464 3/1995

* cited by examiner

Primary Examiner—Steven O. Douglas
Assistant Examiner—Khoa D. Huynh
(74) Attorney, Agent, or Firm—Diller, Ramik & Wight

(57) ABSTRACT

The inventive expansion catheter has a catheter tube (11) and a perfusion tube (12) which can be moved inside the catheter tube (11). The perfusion tube (12) is connected to a stent (13) formed of a wire-type material. The stent (13) is constricted by the catheter tube (11). When, the catheter tube (11) is withdrawn, the stent (13) expands, hereby taking up two expansion areas, (16, 18) which border an area (26) to be protected from the pressure of the blood. A bypass (28) can be fixed in this area (26) by means of an anastomosis (27). The perfusion tube (26) ensures that the blood vessel (21) is supplied behind the obturation point so that the operation can be carried out as non-invasively as possible while the heart is beating.

12 Claims, 2 Drawing Sheets

EXPANSION CATHETER FOR BYPASS SURGERY INCLUDING TWO EXPANSION ZONES AND THEREBETWEEN AN INTERMEDIATE CONSTRICTION

BACKGROUND OF THE INVENTION

The invention relates to an expansion catheter for bypass surgery and serves for insulating the anastomosis region in which a bypass is sewed to a defective blood vessel.

During bypass operations a bypass is connected to a blood vessel displaying a stenosis, the bypass bridging the stenosed section of said blood vessel. Normally the heart is put out of action and the pumping function of the heart is assumed by a heart-lung machine during such an operation so that the surgeon can unimpededly operate the blood vessel. However, operations carried out with the heart put out of action are risky and impose a strain on the patient's body.

In the case of the minimal-invasive bypass surgery the bypass operation is carried out with the heart beating. The connecting point for the bypass is opened by an incision and the bypass is connected there. However, this involves the risk of heavy bleeding; further, the conditions for operations carried out with the heart beating are much harder than those for operations carried out with the heart put out of action.

It is also common practice to dilate blood vessels by a balloon catheter to expand straits. For this purpose perfusion catheters may be used which allow a continuous blood flow through the balloon area to be maintained during dilatation. In this way blocking of the blood vessel concerned during the dilatation is prevented.

In DE 32 35 974 A1 a balloon catheter having two balloons arranged at an axial distance is described. The balloon cathether is adapted to be inserted into a blood vessel. By expanding the balloons the vessel region between the balloons is insulated. To allow the blood to flow the balloon catheter is provided with a perfusion duct bridging the balloon area. Substances are injected into the insulating area which dissolve or pulverize deposits in the vessels.

From DE 195 09 464 C1 a vessel implant is known which comprises an anchoring part and a functional part forming a continuous tubular stent of wire fabric or wire mesh. Between anchoring part and functional part there is a constriction whose walls form a thrombosis filter. The vessel implant is elongated under elastic deformation such that it contracts in radial direction. In this condition it is mounted on a catheter and fixed by means of a supporting tube resting against it from outside. In the blood vessel the implant is released by withdrawing the supporting tube such that the anchoring part can expand and fit from inside to the vessel wall at an elastic bias. Contraction of the vessel implant is not envisaged.

Further, vessel supports are known which are referred to as stents. Such vessel supports are made of wire material. They are inserted by a catheter into the blood vessel and then plastically expanded such that, in the expanded condition, they keep the blood vessel open. Such stents also include reversibly expandable stents. The latter are extended from a catheter tube and then automatically expand due to their elasticity. If the catheter is subsequently mounted on the stent, the stent contracts and is retracted into the catheter tube. Such stents normally serve for expanding a stenosis.

SUMMARY OF THE INVENTION

It is the object of the invention to provide an expansion catheter which can be used to insulate a wall section of a blood vessel without blocking passage of the blood through the blood vessel.

The expansion catheter according to the invention comprises a reversibly expandable stent which, in the expanded condition, has at least two expansion zones space apart from each other and an intermediate constriction. In the expanded condition the expansion zones of the stent are pressed against the vessel wall. Between the two expansion zones the vessel wall is relieved, i. e. it is not subjected to internal pressure. The stent ensures that temporarily no blood pressure acts upon the vessel wall to allow an anastomosis (seam) to be produced on the vessel wall or similar surgical interventions to be performed. The stent is not used as a vessel support but for temporary blocking of the blood flow.

The stent is a latticed metal structure adapted to expand and contract in radial direction. In the expanded condition said metal structure is permeable to blood and thus not suited for complete sealing.

According to a preferred embodiment of the invention the stent is provided with an envelope over at least a portion of its length. Said envelope renders the wall of the stent impermeable to liquids and thus effects a considerable draining of the vessel wall in the constriction area of the stent.

It is of advantage if the stent ends at its distal end in an open expansion zone. This reduces the risk of thrombosis which occurs in the case of formation of heavy eddies caused by the constrictions. Although the blood flow is accelerated when it passes the constriction, it decelerates again inside the distal expansion zone.

After the surgical intervention on the vessel wall the stent contracts again and is retracted into the catheter tube. Thus the stent does not stay in the blood vessel but is removed together with the catheter tube from the patient's body.

The stent may be configured such that it has a shape memory which sets it into the expanded condition unless a restraint is applied from outside. Alternatively, the stent may be configured such that it is set into the expanded condition by application of an external restraint, e. g. by upsetting in axial direction. In any case, the stent comprises at least two expansions zones in the expanded condition.

Hereunder a preferred embodiment of the invention is explained in detail with reference to the drawings in which:

DESCRIPTION OF THE PREFERRED EMBODIMENTS

Figure 1:
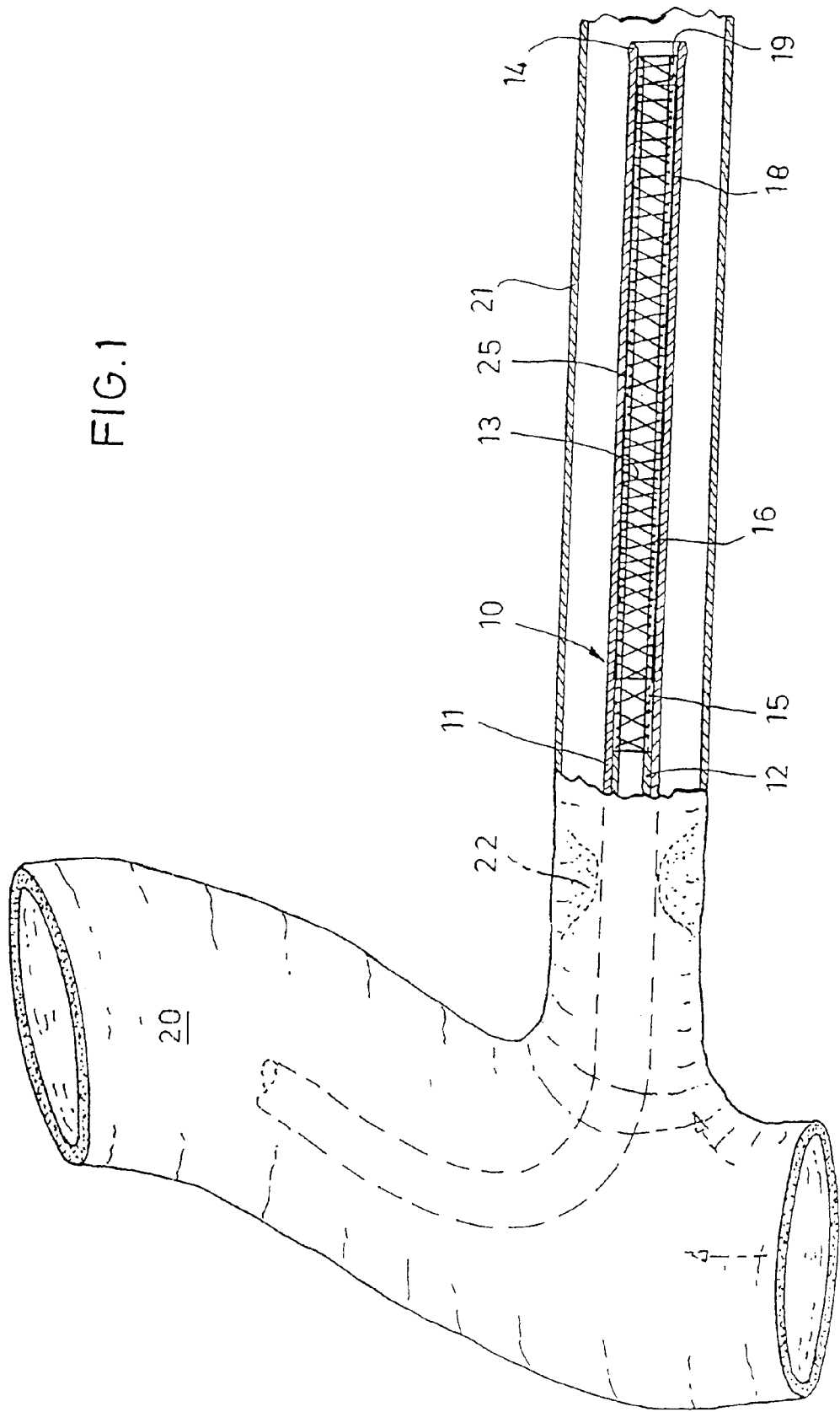
FIG. 1 shows the expansion catheter extending through a stenosis in the coronary artery after having been inserted into the coronary artery.

According to FIG. 1 the expansion catheter 10 comprises an elongate catheter tube 11 whose lumen has a diameter of approximately 1 mm. In the catheter tube 11 a perfusion tube 12 is arranged which is adapted to be displaced in longitudinal direction. At the distal (front) end of the perfusion tube 12 a stent 13 is arranged which extents over a length of approximately 15 mm and which is kept in the compressed condition by the catheter tube 11. The stent 13 has a tubular cross-section. Its wall is made up of a plurality of interconnected webs forming a cellular structure.

By applying the normal technique the catheter tube 11 is inserted into the patient's aorta 20 where a coronary artery 21 branches off. In the example described the coronary artery displays a stenosis 22 which requires a bypass bridging the stenosis to be laid.

The catheter tube 11 passes through the stenosis 22 until its distal end 14 has reached a location spaced from the stenosis 22. Then the perfusion tube 12 with the stent 13 attached thereto is inserted into the catheter tube 11 and advanced until the stent 13 is near the distal end 14 but is still inside the catheter tube. Alternatively, the catheter tube with the perfusion tube 12 and the stent 13 contained therein may be inserted until the condition shown in FIG. 1 has been reached.

Figure 2:
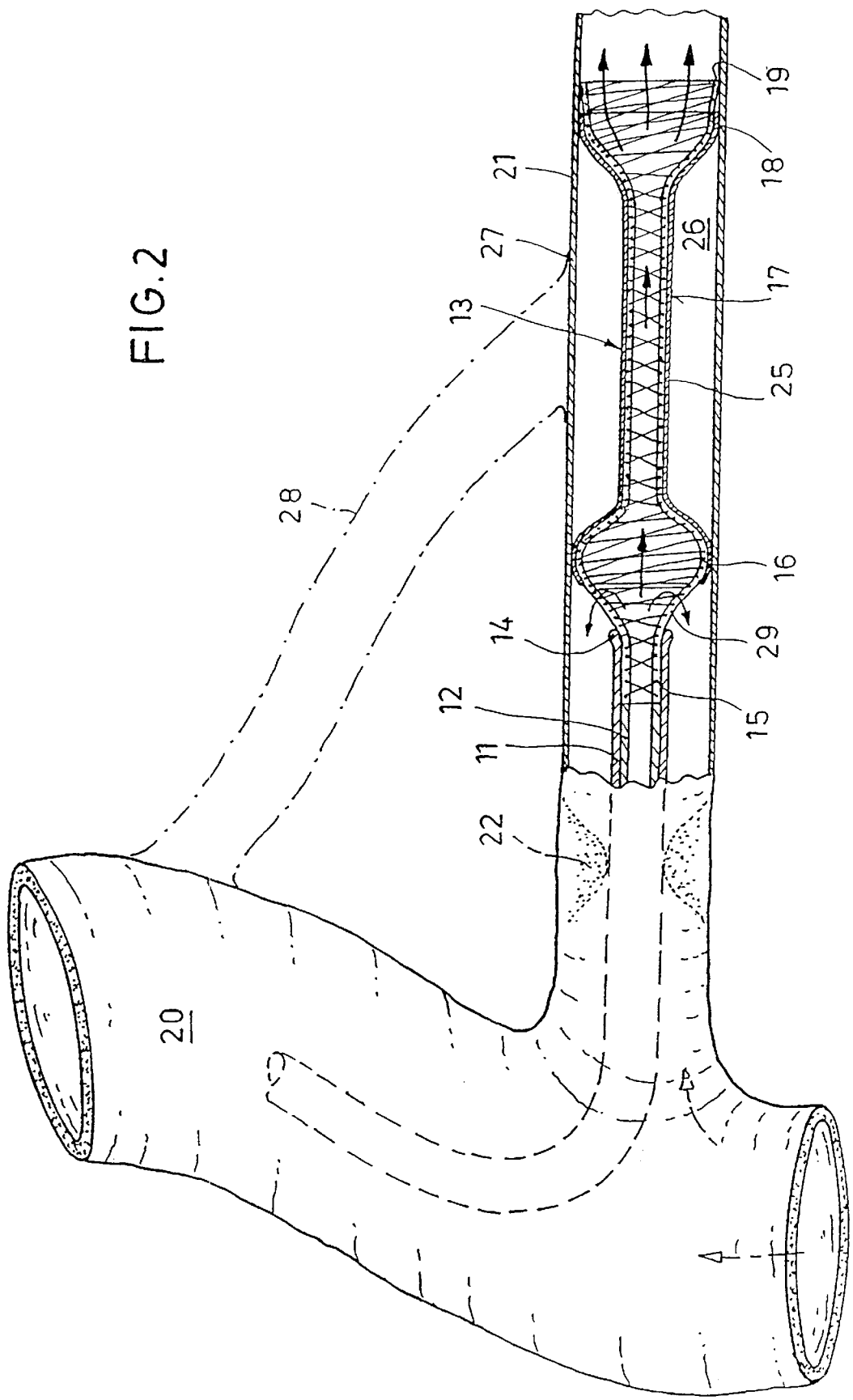
FIG. 2 shows the expansion of the stent for insulating the anastomosis region from the arterial blood pressure.

According to FIG. 2 the catheter tube 11 over the perfusion tube 12 is then withdrawn with the perfusion tube 12 remaining in its position and axially supporting the stent 13. Thus the catheter tube 11 releases the stent 13 so that the latter is no longer constricted from outside but can freely expand to the outside. Merely a short initial area 15 of the stent 13 remains enclosed by the catheter tube.

Adjacent to the initial range 15 the stent 13 comprises an expansion zone 16 in which the stent material is biased to such an extent that it expands to approximately three times the diameter of the original cross-section. Adjacent to the expansion zone 16 a constriction 17 is located where no essential expansion of the stent takes place. At the distal end of the stent another expansion zone 18 is located where the stent widens and ends in an opening 19 of the largest diameter possible. The length of the constriction 17 amounts to approximately three times the diameter of the expansions zones 16 and 18, respectively.

The stent 13 is further provided with an envelope 25 extending from the expansion zone 16 via the constriction 17 to the expansion zone 18 and into the respective expansion areas of the largest diameter possible. The envelope 25 seals the area 26 enclosed by the vessel wall from any blood flow. Therefore an anastomosis 27 can be produced in the area 26, via which a bypass 28 is fixed to the vessel wall. Said bypass 28 comes from the aorta 20 or from the brachial artery and later serves for supplying the coronary vessel 21. The anastomosis can be produced with the heart beating. The perfusion catheter 12 is supplied with blood from its proximal end. The blood flows to the stent 13 and passes through it in longitudinal direction. At the expanded distal end 19 the blood issues over the full cross-section of the blood vessel. Therefore no important eddies and the like, which might result in thrombosis, are produced at the end of the stent.

In the present embodiment the envelope 25 exposes the initial area 29 of the expansion zone 16. Therefore blood may issue from said area 29 and supply the region of the blood vessel behind the stenosis 22 with blood.

In the expanded condition the stent 13 has the shape shown in FIG. 2. It possesses a shape memory and aims at assuming this shape unless it is forced into another shape by restraint from outside. Such a restraint can e. g. be applied by retracting it into the catheter tube 11 with the expansion zones 16,18 being compressed by the catheter tube.

The envelope 25 is a skin surrounding the stent on the outside or on the inside which is impermeable to blood and may be of elastic configuration such that it follows the expansion and contraction movements of the stent. The envelope 25 forms a duct extending over the constriction 17, which ensures the blood supply of the blood vessel portion behind the insulation.

Although a preferred embodiment of the invention has been specifically illustrated and described herein, it is to be understood that minor variations may be made in the apparatus without departing from the spirit and scope of the invention, as defined the appended claims.

What is claimed is:

1. An expansion catheter for bypass surgery of a blood vessel (22) having a circumferential wall (21) comprising a flexible catheter tube (11) and a reversibly expandable stent (13) adapted to be positioned at a distal end (14) of said catheter tube (11), the stent (13) having in its expanded condition at least two expansion zones (16, 18) spaced apart from each and an intermediate constriction (17) therebetween, said stent (13) being provided with a tube-shaped envelope (25) over at least a portion of its length; the stent (13), in its position at said distal end (14), extending in the longitudinal direction of the catheter tube (11) beyond the catheter tube distal end (14) and ending at a distal end (19) of a terminal one (18) of said expansion zones (16, 18) most remote from said catheter tube distal end (14); said intermediate constriction (17) including a longitudinally extending channel (17) having a length which is at least three times greater than the diameter of at least one of the expansion zones (16, 18) in the expanded condition thereof, said channel (17) being substantially smaller in diameter than the expansion zones (16, 18) so that said channel (17) forms within the blood vessel an annular space (26) of substantial volume extending between said expansion zones (16, 18) along which the channel (17) is substantially radially spaced from the wall (21) of the blood vessel (22), said stent distal end (19) defining a diverging opening of said terminal expansion zone (18), and the other terminal expansion zone (16) defining a converging opening (29).

2. The expansion catheter as defined in claim 1 wherein said stent (13) is connected to a perfusion tube (12) extending through the catheter tube (11) which is adapted to be displaced In a longitudinal direction, and a lumen of the perfusion tube (12) communicates with an inside of the stent (13).

3. The expansion catheter as defined in claim 1 wherein the stent (13) is made of elastic material and contracts when being retracted into the catheter tube (11) and expands when being extended from the catheter tube (11).

4. The expansion catheter as defined in claim 1 wherein said stent (13) is connected to a perfusion tube (12) extending through the catheter tube (11) which is adapted to be displaced in a longitudinal direction, and a lumen of the perfusion tube (12) communicates with an inside of the stent (13).

5. The expansion catheter as defined in claim 4 wherein the stent (13) is made of elastic material and contracts when being retracted into the catheter tube (11) and expands when being extended from the catheter tube (11).

6. The expansion catheter as defined in claim 1 wherein the stent (13) is made of elastic material and contracts when being retracted into the catheter tube (11) and expands when being extended from the catheter tube (11).

7. An expansion catheter for bypass surgery of a blood vessel (22) having a circumferential wall (21) comprising a flexible catheter tube (11) and a reversibly expandable stent (13) adapted to be positioned at a distal end (14) of said catheter tube (11), the stent (13) having in its expanded condition at least two expansion zones (16, 18) spaced apart from each and an intermediate constriction (17) therebetween, said stent (13) being provided with a tube-shaped envelope (25) over at least a portion of its length; the stent (13), in its position at said distal end (14), extending in the longitudinal direction of the catheter tube (11) beyond the catheter tube distal end (14) and ending at a distal end

(19) of a terminal one (18) of said expansion zones (16, 18) most remote from said catheter tube distal end (14); said intermediate constriction (17) including a longitudinally extending channel (17) having a length which is at least three times greater than the diameter of at least one of the expansion zones (16, 18) in the expanded condition thereof, said channel (17) being substantially smaller in diameter than the expansion zones (16, 18) and said expansion zones (16, 18) in the expanded conditions thereof being substantially three times the non-expanded diameter thereof so that said channel (17) forms within the blood vessel an annular space (26) of substantial volume extending between said expansion zones (16, 18) along which the channel (17) is substantially radially spaced from the wall (21) of the blood vessel (22), said stent distal end (19) defining a diverging opening of said terminal expansion zone (18), and the other terminal expansion zone (16) defining a converging opening (29).

8. The expansion catheter as defined in claim 7 wherein said stent (13) is connected to a perfusion tube (12) extending through the catheter tube (11) which is adapted to be displaced in a longitudinal direction, and a lumen of the perfusion tube (12) communicates with an inside of the stent (13).

9. The expansion catheter as defined in claim 7 wherein the stent (13) is made of elastic material and contracts when being retracted into the catheter tube (11) and expands when being extended from the catheter tube (11).

10. The expansion catheter as defined in claim 7 wherein said stent (13) is connected to a perfusion tube (12) extending through the catheter tube (11) which is adapted to be displaced in a longitudinal direction, and a lumen of the perfusion tube (12) communicates with an inside of the stent (13).

11. The expansion catheter as defined in claim 10 wherein the stent (13) is made of elastic material and contracts when being retracted into the catheter tube (11) and expands when being extended from the catheter tube (11).

12. The expansion catheter as defined in claim 7 wherein the stent (13) is made of elastic material and contracts when being retracted into the catheter tube (11) and expands when being extended from the catheter tube (11).

* * * * *